US006531146B2

United States Patent
Calhoun et al.

(10) Patent No.: US 6,531,146 B2
(45) Date of Patent: Mar. 11, 2003

(54) RESORBABLE BARRIER MICRO-MEMBRANES FOR ATTENUATION OF SCAR TISSUE DURING HEALING

(75) Inventors: Christopher J. Calhoun, San Diego, CA (US); Ralph E. Holmes, San Diego, CA (US)

(73) Assignee: MacroPore, Inc., San Diego, CA (US)

( * ) Notice: Subject to any disclaimer, the term of this patent is extended or adjusted under 35 U.S.C. 154(b) by 0 days.

(21) Appl. No.: 09/805,411

(22) Filed: Mar. 12, 2001

(65) Prior Publication Data

US 2002/0001609 A1 Jan. 3, 2002

Related U.S. Application Data

(60) Provisional application No. 60/231,800, filed on Sep. 11, 2000, and provisional application No. 60/196,869, filed on Mar. 10, 2000.

(51) Int. Cl.[7] ............................. A61F 2/02; A61K 47/30
(52) U.S. Cl. ..................................... 424/426; 514/772.3
(58) Field of Search ......................... 424/426; 514/772.3

(56) References Cited

U.S. PATENT DOCUMENTS 5,486,593 A  * 1/1996 Tang et al. ................. 528/370

* cited by examiner

Primary Examiner—Carlos Azpuru
(74) Attorney, Agent, or Firm—Stout, Uka, Buyan & Mullins, LLP (57) ABSTRACT

Resorbable polylactide polymer scar tissue reduction barrier membranes and methods of their application are disclosed. The scar-tissue reduction barrier membranes are constructed entirely of polylactide resorbable polymers, which are engineered to be absorbed into the body relatively slowly over time in order to reduce potential negative side effects. The scar tissue reduction barrier membranes are formed to have thicknesses on the order of microns, such as, for example, thicknesses between 10 and 300 microns. The membranes are preshaped with welding flanges and stored in sterile packaging.

32 Claims, 12 Drawing Sheets

RESORBABLE BARRIER MICRO-MEMBRANES FOR ATTENUATION OF SCAR TISSUE DURING HEALING

RELATED APPLICATIONS

This application claims the benefit of priority under 35 U.S.C. section 119(e) of provisional application No. 60/231,800, filed Sep. 11, 2000, and of provisional application No. 60/196,869, filed Mar. 10, 2000.

FIELD OF THE INVENTION

The present invention relates generally to medical devices and, more particularly, to devices and methods for attenuating the formation of post-surgical adhesions between a post-surgical site and adjacent surrounding tissue.

BACKGROUND OF THE INVENTION

A major clinical problem relating to surgical repair or inflammatory disease is adhesion which can occur during the initial phases of the healing process after surgery or disease. Adhesion is a condition which involves the formation of abnormal tissue linkages. These linkages can for example impair bodily function, produce infertility, obstruct the intestines and other portions of the gastrointestinal tract (bowel obstruction) and produce general discomfort, e.g. pelvic pain. The condition can in some instances be life threatening. The most common form of adhesion occurs after surgery as a result of surgical interventions, although adhesion may occur as a result of other processes or events such as pelvic inflammatory disease, mechanical injury, radiation treatment and the presence of foreign material.

Various attempts have been made to prevent postoperative adhesions. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (membranes, gels or solutions) aiming to minimize apposition of serosal surfaces, have all been attempted. Unfortunately, limited success has been seen with these methods. Barrier materials, in various forms such as membranes and viscous intraperitoneal solutions, which are designed to limit tissue apposition, have also met with only limited success. A few of these barrier materials include cellulosic barriers, polytetrafluoroethylene materials, and dextran solutions.

U.S. Pat. No. 5,795,584 to Tokahura et al. discloses anti-adhesion or scar tissue reduction films or membranes, and U.S. Pat. No. 6,136,333 to Cohn et al. discloses similar structures. In the Tokahura et al. patent, a bioabsorbable polymer is copolymerized with a suitable carbonate and then formed into a non-porous single layer adhesion barrier, such as a film. In the Cohn et al. patent a polymeric hydrogel for anti-adhesion is formed without crosslinking by using urethane chemistry. Both of these patents involve relatively complex chemical formulas and/or reactions to result in particular structures to be used as surgical adhesion barriers.

SUMMARY OF THE INVENTION

Resorbable polylactide polymer scar tissue reduction barrier membranes and methods of their application have been discovered. In accordance with one aspect of the present invention, the scar-tissue reduction barrier membranes are constructed entirely of polylactide resorbable polymers, which are engineered to be absorbed into the body relatively slowly over time in order to reduce potential negative side effects. The scar tissue reduction barrier membranes are formed to have thicknesses on the order of microns, such as, for example, thicknesses between 10 and 300 microns. The membranes are preshaped with welding flanges and stored in sterile packaging.

BRIEF DESCRIPTION OF THE DRAWINGS

FIG. 6b is a cross-sectional view of the scar-reduction resorbable barrier membrane shown in FIG. 6a;

FIG. 7a is a top planar view of a scar-reduction resorbable barrier membrane in accordance with a fifth pre-formed embodiment of the present invention;

FIG. 7b is a cross-sectional view of the scar-reduction resorbable barrier membrane shown in FIG. 7a;

FIG. 8b is a cross-sectional view of the scar-reduction resorbable barrier membrane shown in FIG. 8a;

FIG. 9b is a cross-sectional view of the scar-reduction resorbable barrier membrane shown in FIG. 9a;

FIG. 10b is a cross-sectional view of the scar-reduction resorbable barrier membrane shown in FIG. 10a;

FIG. 11b is a cross-sectional view of the scar-reduction resorbable barrier membrane shown in FIG. 11a;

FIG. 12b is a cross-sectional view of the scar-reduction resorbable barrier membrane shown in FIG. 12a;

FIG. 13b is a cross-sectional view of the scar-reduction resorbable barrier membrane shown in FIG. 13a;

FIG. 14b is a cross-sectional view of the scar-reduction resorbable barrier membrane shown in FIG. 14a;

FIG. 15b is a cross-sectional view of the scar-reduction resorbable barrier membrane shown in FIG. 15a;

FIG. 16b is a cross-sectional view of the scar-reduction resorbable barrier membrane shown in FIG. 16a;

FIG. 17b is a cross-sectional view of the scar-reduction resorbable barrier membrane shown in FIG. 17a.

DESCRIPTION OF THE PRESENTLY PREFERRED EMBODIMENTS

The present invention provides a resorbable implant in membrane form that can be used in various surgical contexts to retard or prevent tissue adhesions, and reduce scarring. The polylactide polymers and co-polymers of the present invention require relatively simple chemical reactions and formulations. It is believed that the present scar-reduction resorbable barrier membranes of polylactide polymers and co-polymers can induce relatively minor localized tissue inflammation, but that inflammation is believed to be minimized as a result of the presently engineered compositions, constructions, and applications as set forth herein, to thereby yield highly effective scar tissue reduction.

The scar-reduction resorbable barrier membrane of the present invention may be more effective than other membranes because it is very smooth and non-porous. Moreover, the barrier membrane is preferably bioabsorbable in the body. The lack of porosity acts to form a barrier that does not allow interaction of the tissues. The non-porosity and the smoothness of the barrier membrane can reduce tissue turbulence, enhance tissue guidance, and minimize scar formation. Moreover, the smooth, uninterrupted surface of the barrier membrane material may facilitate movement of the dura and local tissues across the area, hence reducing frictional rubbing and wearing which may induce scar tissue formation.

As used herein, the term "non-porous" refers to a material which is generally water tight and, in accordance with a preferred embodiment, not fluid permeable. However, in a modified embodiment of the invention micro-pores (i.e., fluid permeable but not cell permeable) may exist in the scar-reduction resorbable barrier membrane of the present invention, to the extent, for example, that they do not substantially disrupt the smoothness of the surfaces of the resorbable barrier membrane to cause scarring of tissue. In substantially modified embodiments for limited applications, pores which are cell permeable but not vessel permeable may be manufactured and used. As presently preferred, the resorbable barrier membrane is manufactured using a press molding procedure to yield a substantially non-porous film. The barrier membrane materials of present invention may have a semi-rigid construction, and are fully contourable when heated to approximately 55 degrees Celsius. As presently embodied, many of the thinner membrane thicknesses can be sufficiently contoured even in the absence of heating.

The material can be used in a number of surgical applications, including: surgical repair of fracture orbital floors, surgical repair of the nasal septum and perforated ear drum barrier membrane, as a protective sheathing to facilitate osteogenesis, surgical repair of the urethral anatomy and repair of urethral strictures, prevention of synostosis in completed corrective surgery for cranial fusions and forearm fractures, lessening of soft-tissue fibrosis or bony growth, as a temporary covering for prenatal rupture omphalocele during staged repair procedures, guided tissue regeneration between the teeth and gingival margin, tympanic membrane repairs, dural coverings and neural repair, heart vessel repair, hernia repair, tendon anastomoses, temporary joint spacers, wound dressings, scar coverings, and as a covering for gastroschisis. The barrier membrane material of the present invention is particularly suitable for preventing tissue from abnormally fibrotically joining together following surgery, which can lead to abnormal scarring and interfere with normal physiological functioning. In some cases, such scarring can force and/or interfere with follow-up, corrective, or other surgical operations.

For example, there is evidence pointing to epidural adhesions as possible factors contributing to failed back surgery. Epidural fibrosis may occur following spinal injuries or as a post-operative surgical complication. The dense scar formation on dura and around nerve roots has previously been described as the "laminotomy membrane," and has been implicated in rendering subsequent spine operations technically more difficult. In a lamininectomy procedure, for example, the scar-reduction resorbable barrier membrane of the present invention is desirably inserted between the dural sleeve and the paravertebral musculature post laminotomy and conforms readily to block exposed marrow elements of the laminae. Imposition of the membrane material as a barrier between the paravertebral musculature and the epidural space is believed to reduce cellular trafficking and vascular invasion into the epidural space from the overlying muscle and adjacent exposed cancellous bone. Moreover, tests have shown that the present barrier membrane material does not appear to interfere with normal posterior wound healing while at the same time inhibiting the unwanted adhesions and scarring.

In a preferred embodiment of the present invention, the barrier membrane material comprises a poly lactide polymer or co-polymer and, more preferably, comprises poly (L-lactide-co-D,L-lactide) 70:30 Resomer LR708 manufactured and supplied from Boehringer Ingelheim KG of Germany. A preformed membrane made from the material can be shaped at the time of surgery by bringing the material to its glass transition temperature, using heating iron, hot air, heated sponge or hot water bath methods. The scar-tissue reduction barrier membrane of the present invention preferably has a uniform thickness of less than about 300 microns, preferably less than 200 microns, and more preferably between 10 microns and 100 microns. As defined herein, the "micro-membranes" of the present invention comprise thicknesses between 10 microns and 300 microns and, preferably, between 10 and 100 microns.

The very thin construction of these micro-membranes is believed to substantially accelerate the rate of absorption of the implants, compared to rates of absorption of thicker membrane implants of the same material. It is believed, however, that resorption into the body too quickly of the micro-membrane will yield undesirable drops in local pH levels, thus introducing/elevating, for example, local inflammation, discomfort and/or foreign antibody responses. Further, a resulting uneven (e.g., cracked, broken, roughened or flaked) surface of a barrier membrane degrading too early may undesirably cause tissue turbulence between the tissues before, for example, adequate healing has occurred, resulting in potential tissue inflammation and scarring. It is believed that a micro-membrane of the present invention having a thickness of about 200 microns or less should maintain its structural integrity for a period in excess of three weeks and, more preferably for at least 7 weeks, before substantially degrading, so that the anti-scarring function can be achieved and optimized. To the extent the micro-membrane does not degrade at an accelerated rate, compared to a thicker membrane of the same material, the membrane should maintain its structural integrity for a period in excess of 6 months and, more preferably for at least one year, before substantially degrading, in order to achieve and optimize the anti-scarring function. The polylactide resorbable polymer barrier membranes in accordance with this aspect of the present invention are thus designed to resorb into the body at a relatively slow rate.

The object of reducing acidity levels and/or tissue turbulence, and any accompanying inflammation (e.g., swelling), at the post-surgical site is believed to be of particular importance in the context of spinal surgeries, which are often performed for the very purpose of relieving inflammation-induced discomfort. It is believed that nerve tissue can be particularly sensitive to, for example, slightly elevated acidity levels and inflammation. During a typical spinal surgical procedure, such as, for example, a laminotomy, a portion of the lamina structure is removed from a patient's vertebrae in order to, for example, provide access to the spinal column and/or disk.

The barrier membrane material may be provided in rectangular membranes that are for example several centimeters on each side, or can be cut and formed into specific shapes, configurations and sizes by the manufacturer before packaging and sterilization. In modified embodiments, various known formulations and copolymers of poly lactides may affect the physical properties of the scar-reduction resorbable barrier membrane and/or the bridging membrane. The thin barrier membranes of the present invention are sufficiently flexible to conform around anatomical structures, although some heating in a hot water bath may be necessary for thicker configurations. In modified embodiments, certain poly lactides which become somewhat more rigid and brittle at thicknesses above 0.25 mm and which can be softened by formation with a copolymer and another polylactide, for example, may be implemented to form scar-reduction resorbable barrier micro-membrane. Moreover, in accordance with another aspect of the present invention, the scar-tissue reduction barrier micro-membrane and/or the bridging membrane, (defined infra) may comprises a substance for cellular control, such as at least one of a chemotactic substance for influencing cellmigration, an inhibitory substance for influencing cell-migration, a mitogenic growth factor for influencing cell proliferation, a growth factor for influencing cell differentiation, and factors which promote neoangiogenesis (formation of new blood vessels).

Figure 1:
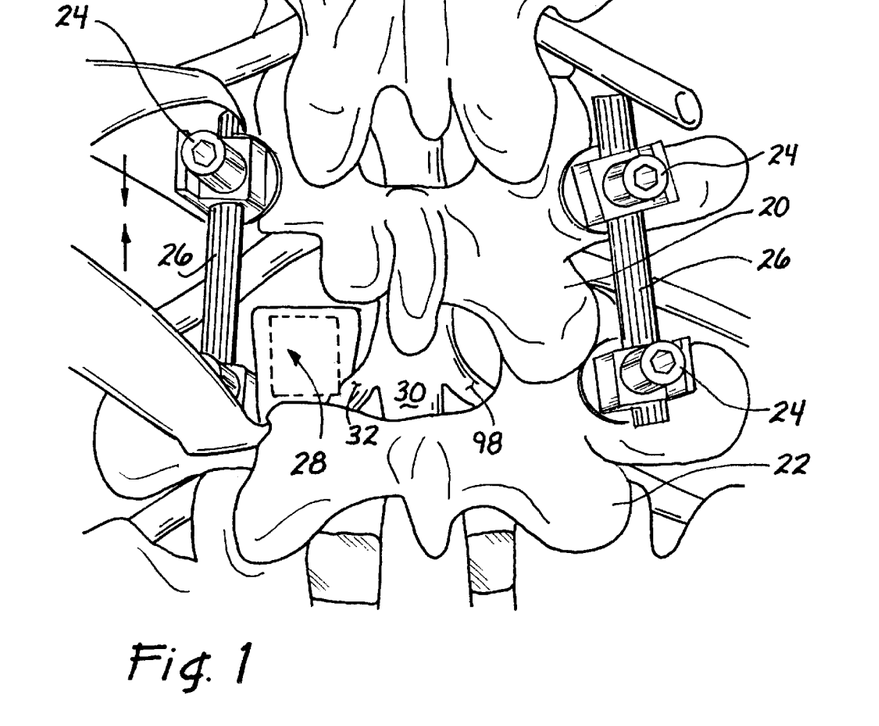
FIG. 1 illustrates a laminotomy procedure wherein a portion of the posterior arch (lamina) of a vertebra is surgically removed.
Figure 2:
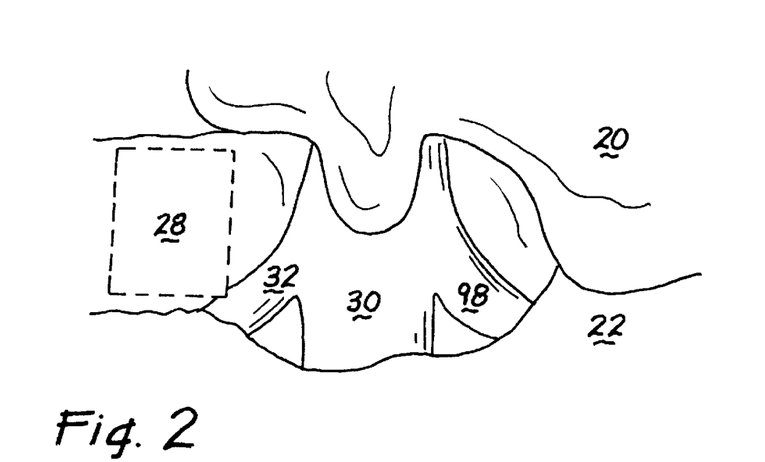
FIG. 2 is an enlarged view of FIG. 2.

Referring more particularly to the drawings, FIG. 1 illustrates a laminotomy procedure wherein a the two vertebrae 20 and 22 are separated and fixated using screws 24 and rods 26, and a portion of the lamina has been removed, leaving a window 28 (shown as a phantom rectangle) in the vertebrae 22. FIG. 2 is an enlarged view of the window 28 in the lamina of the vertebrae 22. The spinal chord 30 and an exiting nerve root 32 are thus exposed. In accordance with the present invention, the scar-reduction resorbable barrier micro-membrane is applied to the dura of both the spinal chord 30 and the exiting nerve root 32, to thereby attenuate or eliminate the occurrence of post-operative scarring in the vicinity of the exiting nerve root 32. In a modified embodiment, a thicker bridging membrane is applied to one or both of the vertebrae 20 and 22, to thereby bridge (i.e., tent) over and cover the window 28. This bridging membrane may be non-porous, fluid permeable, cell permeable or vessel permeable in accordance with various embodiments, and preferably comprises a thickness between about 0.5 mm and 2.0 mm for preventing prolapse of adjacent muscle tissue into the foramen (i.e., the spinal lumen containing the spinal chord 30 and exiting nerve root 32). In accordance with various embodiments, the bridging membrane may be used alone or in combination with the scar-reduction resorbable barrier micro-membrane or, the scar-reduction resorbable barrier membrane may be used without the bridging membrane.

Various means for attaching the barrier membrane to structures such as muscular tissue, other soft tissue, or bone are contemplated. For example, sutures or staples may be used to attach the membrane to the paravertebral muscle. As another example, the bridging membrane in particular may be secured to the vertebrae bone using resorbable bone screws or tacks. Tucking or folding the membrane material into anatomical crevices may be sufficient to fix its position. An adhesive such as a fibrin sealant, or a resorbable cyanoacrylate adhesive may further be utilized to secure the membranes, alone or in combination with the above means of attachment.

In accordance with one aspect of the present invention, the scar-reduction resorbable barrier micro-membrane can be heat bonded, such as with a bipolar electro-cautery device, ultrasonicly welded, or similarly sealed directly to the dura of the spinal chord 30 and the exiting nerve root 32. Such a device can be used to heat the barrier membrane at various locations, such as at the edges and at points in the middle, at least above its glass transition temperature, and preferably above its softening point temperature. The glass transition temperature of the preferred material is about 55° Celsius, while its softening point temperature is above 110° Celsius. The material is heated along with adjacent tissue such that the two components bond together at their interface. In another embodiment, the scar-reduction resorbable barrier membrane can be heat bonded or sealed directly to one or both of the vertebrae 20 and 22, or to muscle or other soft tissue, for example. In yet another embodiment, the scar-reduction resorbable barrier micro-membrane can be heat bonded or sealed directly to itself in an application, for example, wherein the micro-membrane is wrapped around a structure and then heat joined to itself. Moreover, the technique of heat-sealing the barrier membrane material to itself or body tissue may be combined with another attachment method for enhanced anchoring. For example, the barrier membrane material may be temporarily affixed in position using two or more points of heat sealing (i.e., heat welding) using an electro-cautery device, and sutures, staples or glue can then be added to secure the barrier membrane into place.

Figures 3, 4, 5:
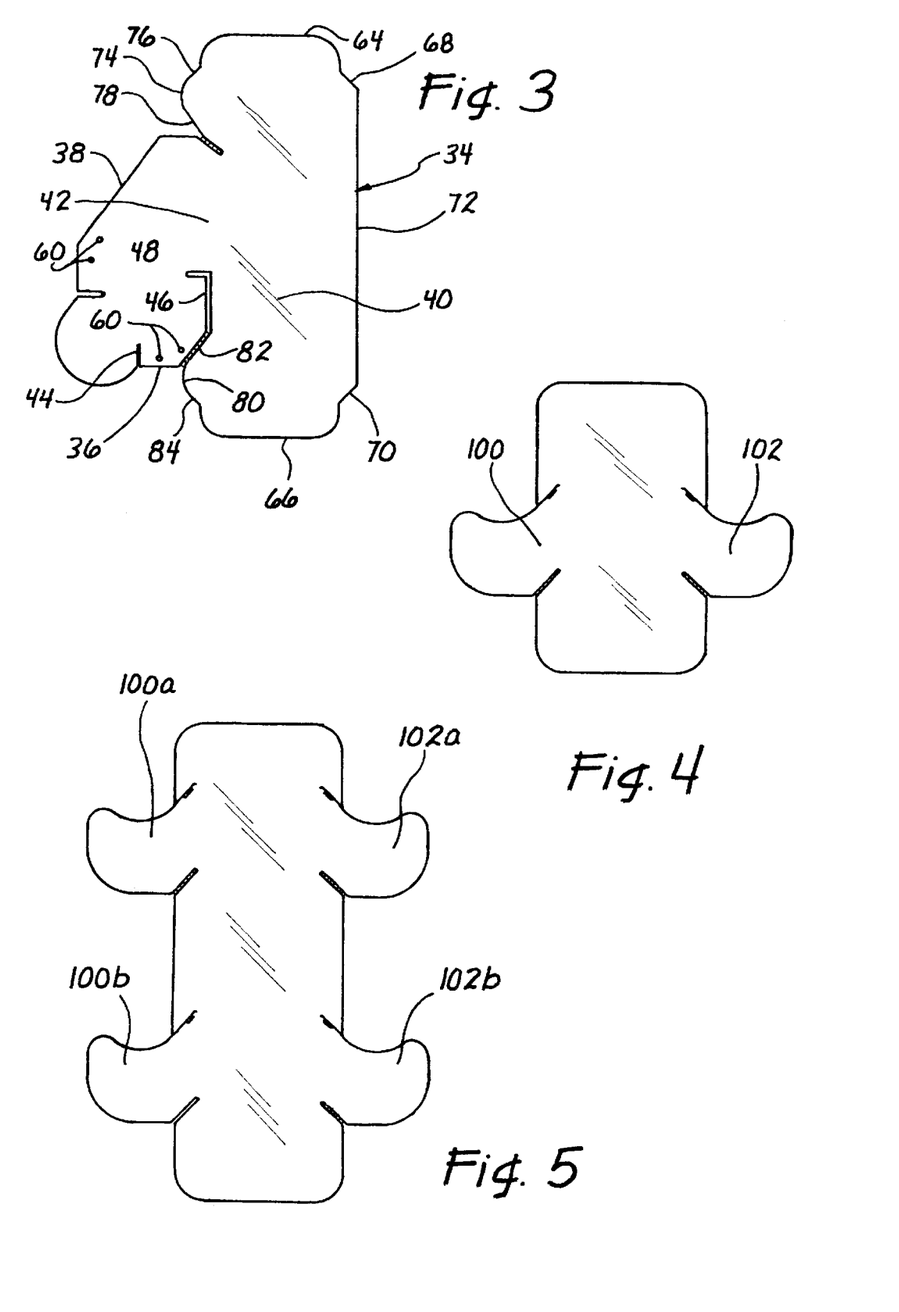
FIG. 3 illustrates a scar-reduction resorbable barrier micro-membrane for application to the exiting nerve root of the spinal chord in accordance with a first pre-formed embodiment of the present invention.
FIG. 4 illustrates a scar-reduction resorbable barrier micro-membrane for application to two exiting nerve roots of the spinal chord in accordance with a second pre-formed embodiment of the present invention.
FIG. 5 illustrates a scar-reduction resorbable barrier micro-membrane for application to four exiting nerve roots of the spinal chord in accordance with a third pre-formed embodiment of the present invention.
Figure 6A:
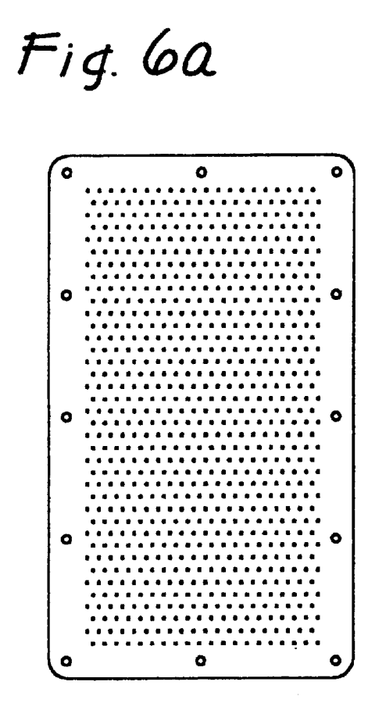
FIG. 6a is a top planar view of a scar-reduction resorbable barrier membrane in accordance with a fourth pre-formed embodiment of the present invention.
Figure 6B:
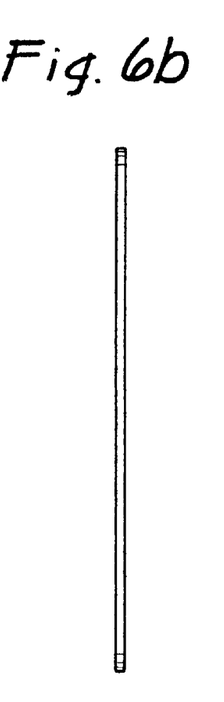
Figures 7A, 7B:
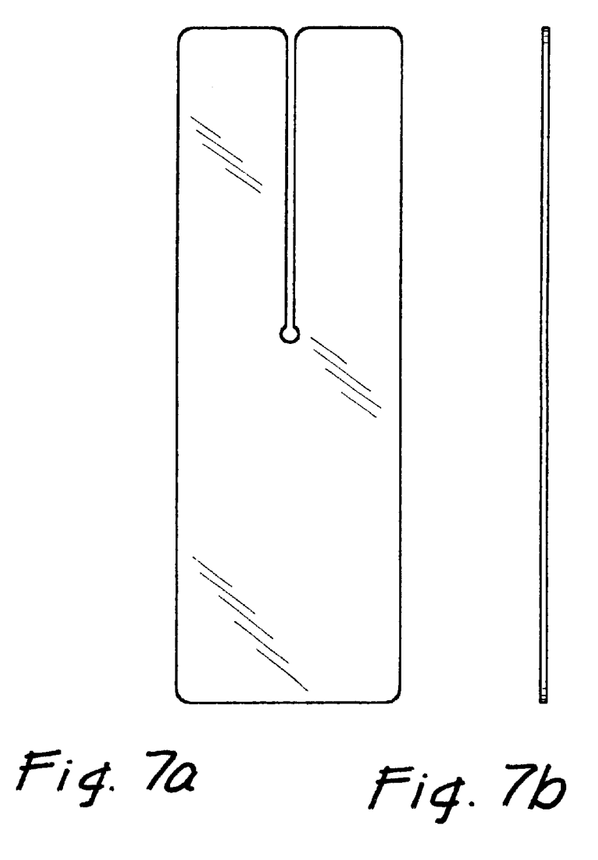
Figure 8A:
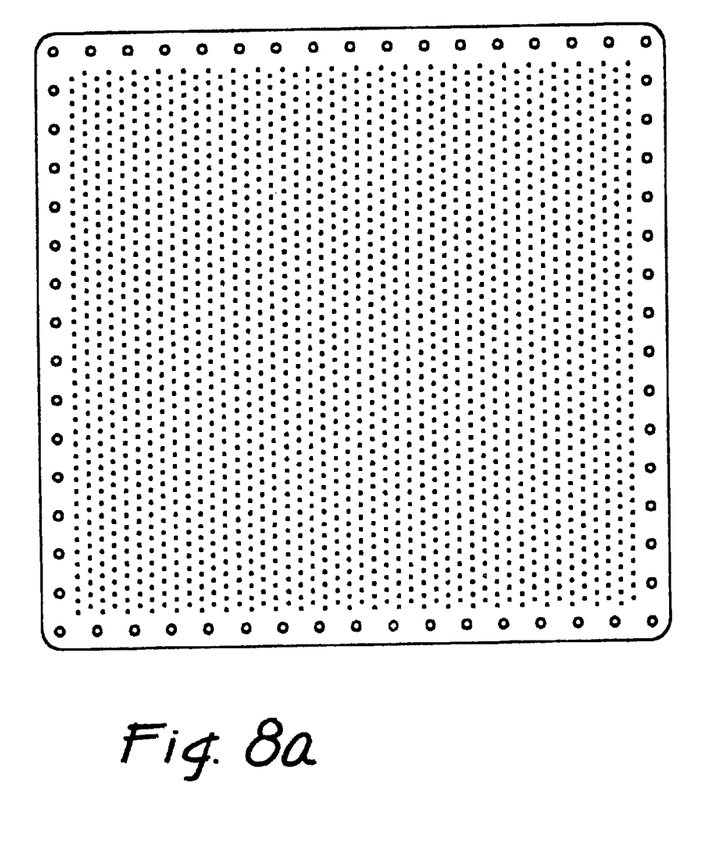
FIG. 8a is a top planar view of a scar-reduction resorbable barrier membrane in accordance with a sixth pre-formed embodiment of the present invention.
Figure 8B:
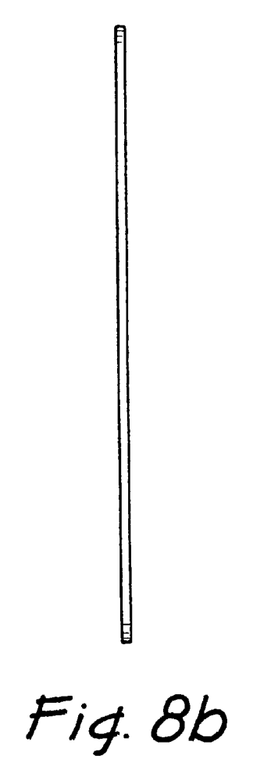
Figure 9A:
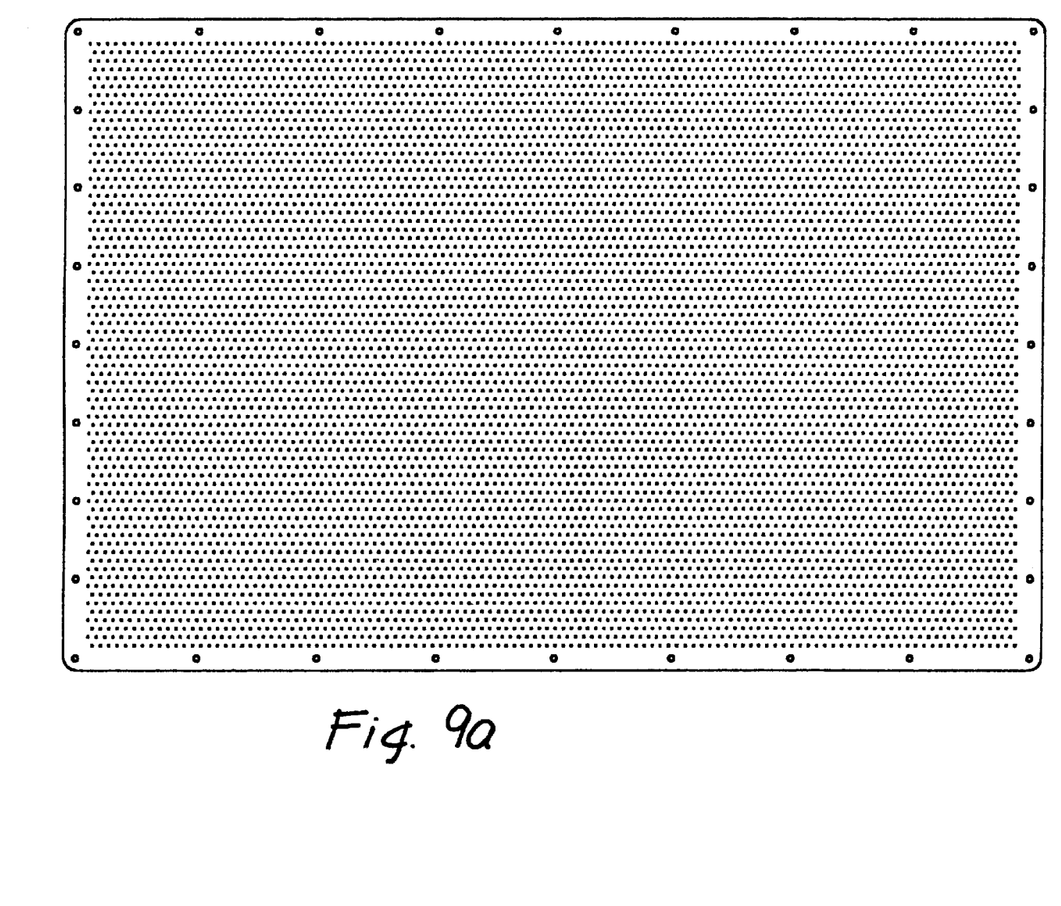
FIG. 9a is a top planar view of a scar-reduction resorbable barrier membrane in accordance with a seventh pre-formed embodiment of the present invention.
Figure 9B:
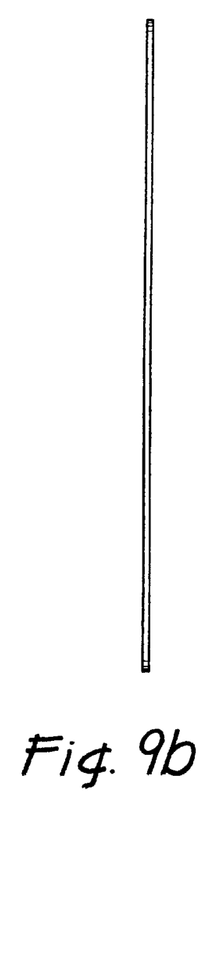
Figure 10A:
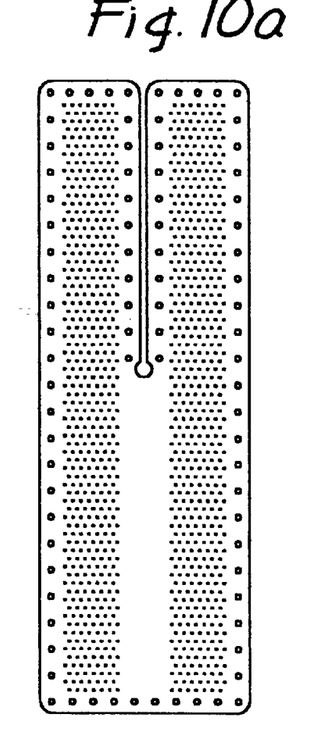
FIG. 10a is a top planar view of a scar-reduction resorbable barrier membrane in accordance with an eighth pre-formed embodiment of the present invention.
Figure 10B:
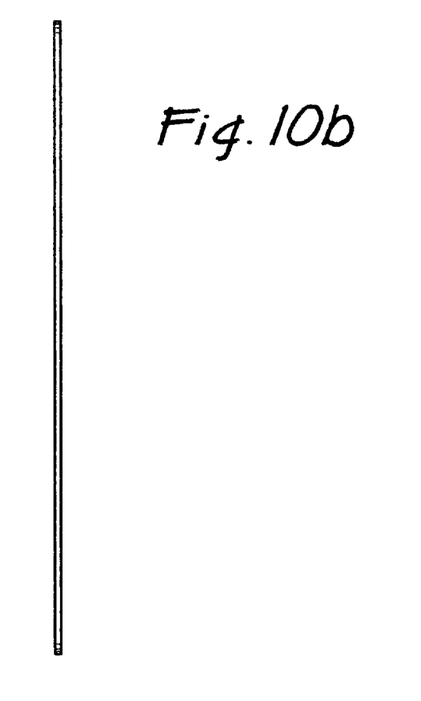
Figure 11A:
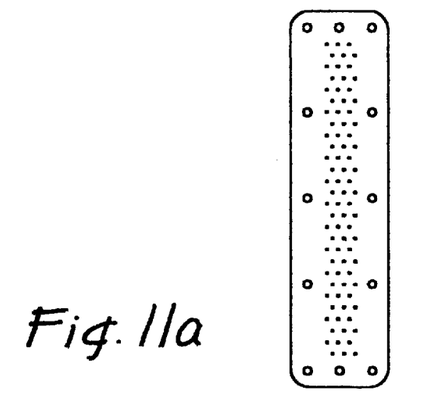
FIG. 11a is a top planar view of a scar-reduction resorbable barrier membrane in accordance with a ninth pre-formed embodiment of the present invention.
Figure 11B:
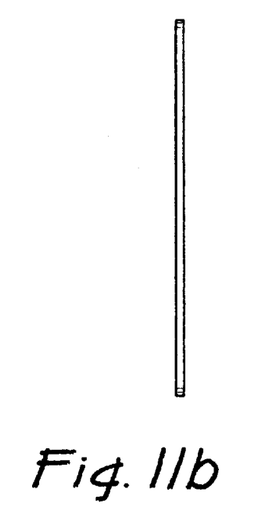
Figure 12A:
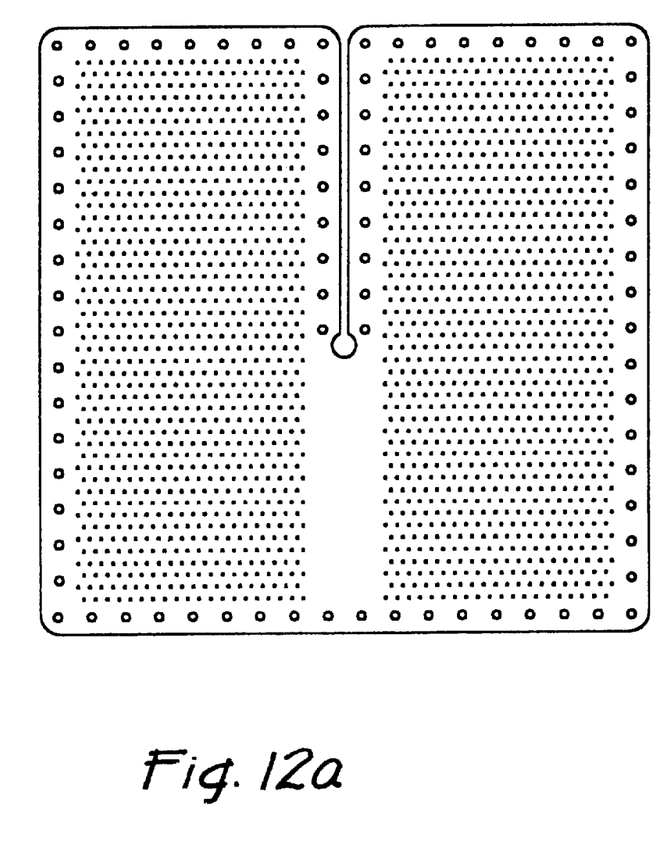
FIG. 12a is a top planar view of a scar-reduction resorbable barrier membrane in accordance with a tenth pre-formed embodiment of the present invention.
Figure 12B:
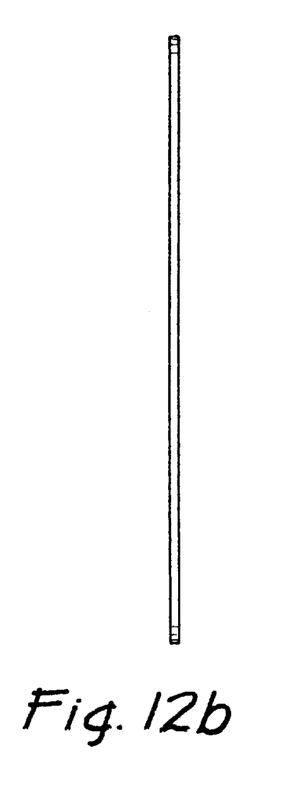
Figure 13A:
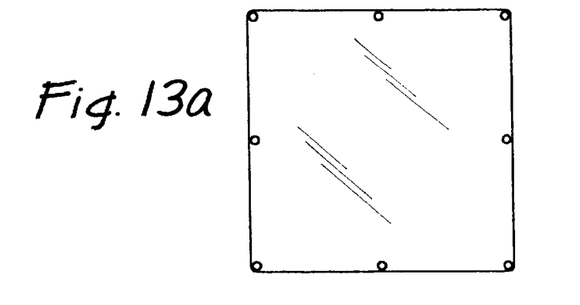
FIG. 13a is a top planar view of a scar-reduction resorbable barrier membrane in accordance with an eleventh pre-formed embodiment of the present invention.
Figure 13B:
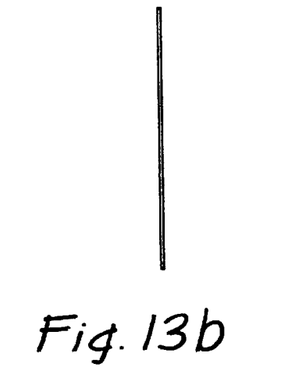
Figure 14A:
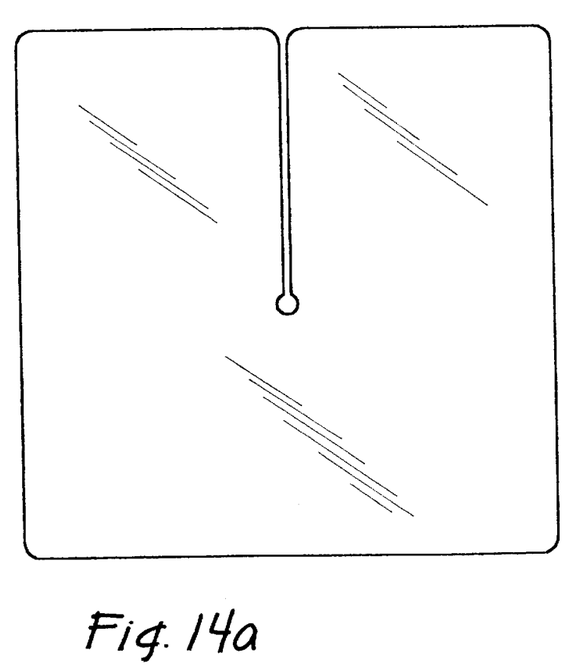
FIG. 14a is a top planar view of a scar-reduction resorbable barrier membrane in accordance with a twelfth preformed embodiment of the present invention.
Figure 14B:
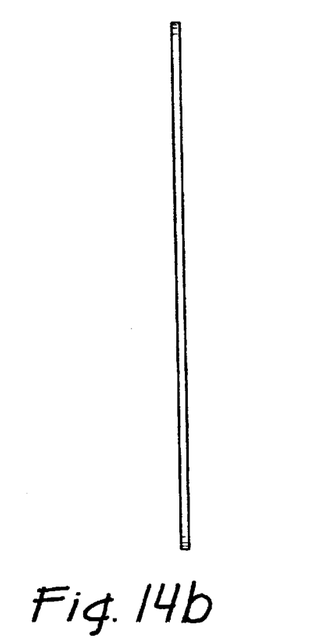
Figure 15A:
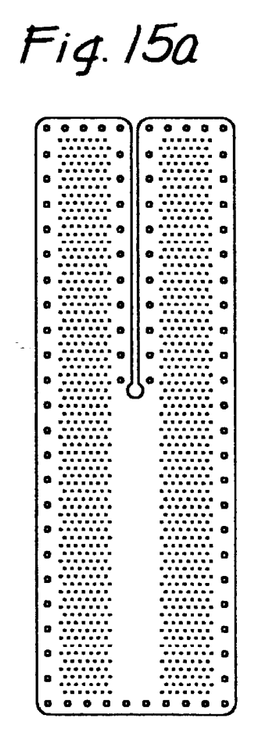
FIG. 15a is a top planar view of a scar-reduction resorbable barrier membrane in accordance with a thirteenth pre-formed embodiment of the present invention.
Figure 15B:
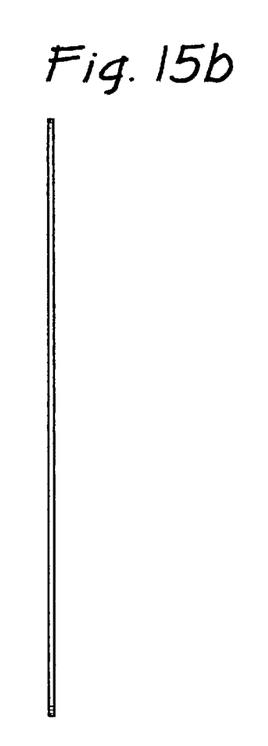
Figure 16A:
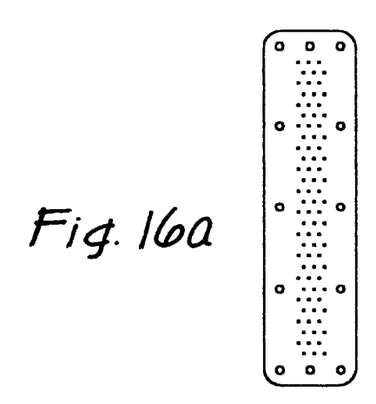
FIG. 16a is a top planar view of a scar-reduction resorbable barrier membrane in accordance with a fourteenth pre-formed embodiment of the present invention.
Figure 16B:
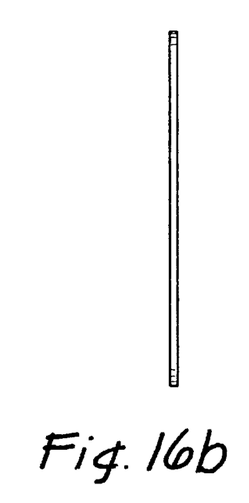
Figure 17A:
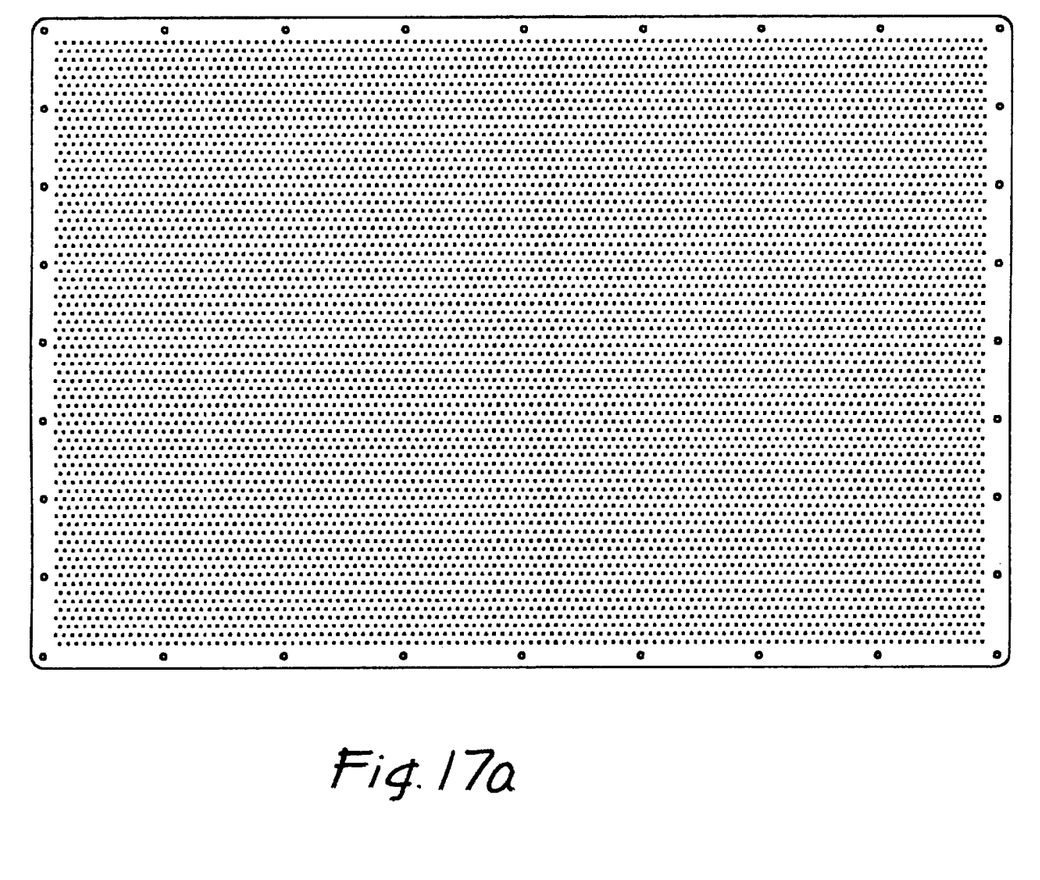
FIG. 17a is a top planar view of a scar-reduction resorbable barrier membrane in accordance with a fifteenth preformed embodiment of the present invention.
Figure 17B:
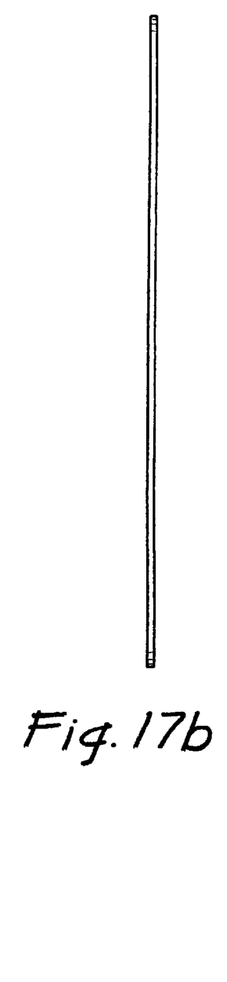
Figure 18:
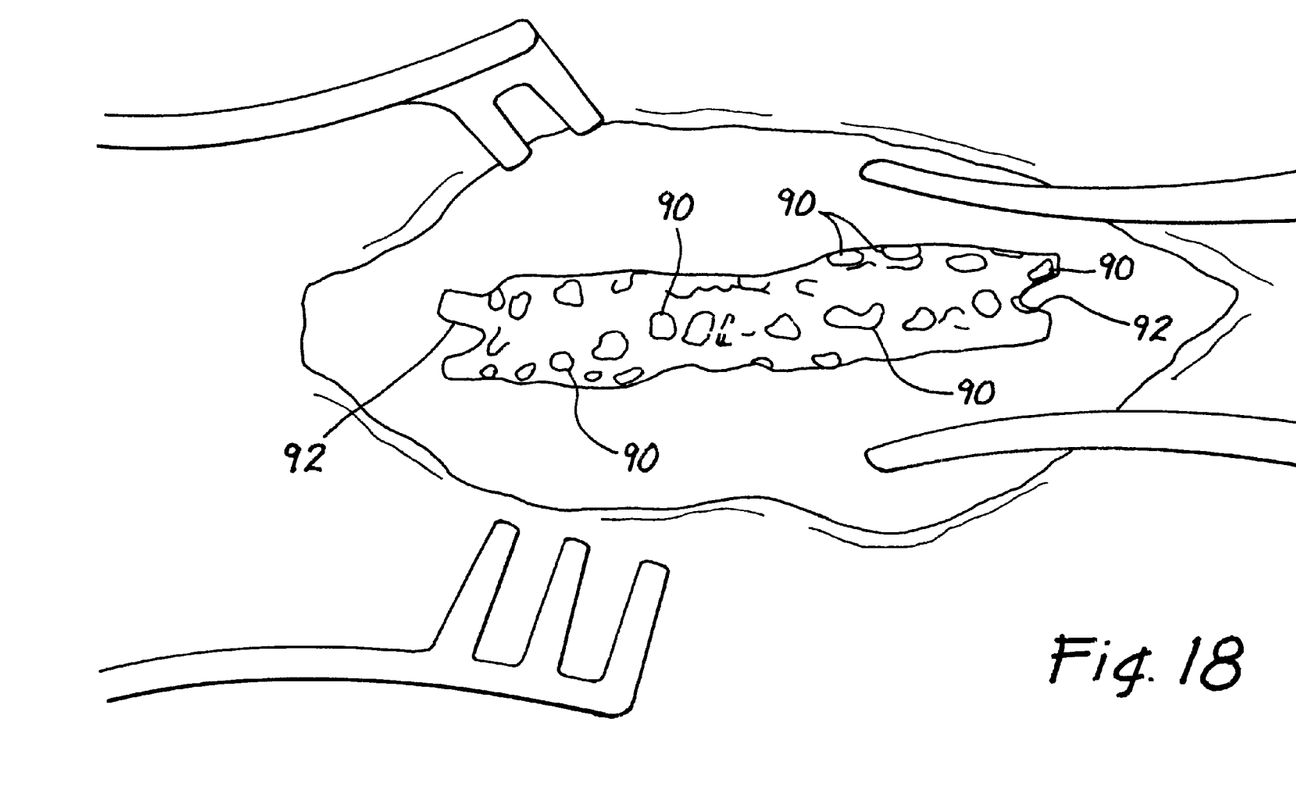
FIG. 18 is illustrates a scar-reduction resorbable barrier micro-membrane of the present invention implanted on a rat spine, with two spinus processes of the spine protruding at opposing ends of the implant.

Turing to FIG. 3, a pre-formed scar-reduction resorbable barrier micro-membrane 34 is formed with a first welding flange 36 and a second welding flange 38 thereon. A trunk portion 40 fits over the spinal chord 30, and a branch portion 42 fits over the exiting nerve root 32. The first welding flange 36 is formed by a first slit 44 and a second slit 46, and the second welding flange 38 is formed by a first slit 48 and a second slit 50. In application, the pre-formed scar-reduction resorbable barrier micro-membrane 34 is placed over the spinal chord 30 and the exiting nerve root 32 and, subsequently, the first welding flange 36 and the second welding flange 38 are bent at least partially around the exiting nerve root. The rounded end 52 of the branch portion 42 fits onto a portion of the exiting nerve root 32 furthest away from the spinal chord 30. As presently embodied, The first welding flange 36 and the second welding flange are wrapped around, and preferably racked beneath (i.e., behind) the exiting nerve root 32. In a preferred embodiment, the first welding flange 36 is then heat welded to the second welding flange 38. The flanges preferably are cut to wrap entirely around the exiting nerve root 32 and overlap one another. The first welding flange 36 may be sutured to the second welding flange 38, alone or in addition with the heat welding step, to thereby secure the first welding flange 36 to the second welding flange 38. In another embodiment, neither heat welding nor suturing are used and the flanges are merely tucked partially or completely around the exiting nerve root 32 (depending on the dimensions of the root 32). When sutures are to be used, the pre-formed scar-reduction resorbable barrier micro-membrane 34 may be pre-formed ad packaged with optional suture apertures 60. The edges 64 ad 66 are then preferably heat welded to the spinal chord 30. The two edges 68 and 70 form a third welding flange 72. A fourth welding flange 74 is formed by slits 76 and 78, and a fifth welding flange 80 is formed by slits 82 and 84. The welding flanges may be secured it manners similar to those discussed in connection with the welding flanges 36 and 38. Heat welds may further be secured along other edges and along the surface of the pre-formed scar-reduction resorbable barrier micro-membrane 34, such as shown at 90 in FIG. 18. Moreover, notches may be formed on the membranes of the present invention, such as, for example, at the ends 64 and 66 in modified-shape embodiments, for accommodating, for example, the spinal processes. Such exemplary notches are shown in FIG. 18 at 92.

FIG. 4 illustrates a scar-reduction resorbable barrier micro-membrane for application to two exiting nerve roots 32 and 98 of the spinal chord in accordance with another pre-formed embodiment of the present invention. FIG. 5 illustrates a scar-reduction resorbable barrier micro-membrane similar to that of FIG. 4 but adapted for application to four exiting nerve roots of the spinal chord in accordance with another pre-formed embodiment of the present invention. For example, the branch portion 100 is analogous in structure and operation to the branch portion 42 of the FIG. 3 embodiment, and the other branch portion 102 is constructed to accommodate the exiting nerve root 98. Simlar elements are shown in FIG. 5 at 100a, 102a, 100b and 102c. The embodiments of FIGS. 6–17 illustrate other configurations for accommodating different anatomical structures. For example, the configurations of FIGS. 7, 10, 12, 14 and 15 are designed to be formed into, for example, a cone structure to fit around a base portion with a protrusion extending through the center of the membrane. The illustrated embodiments of FIGS. 6–17 have suture perforations formed around their perimeters, and many are shown with cell and vessel permeable pores.

In accordance with the present invention, the pre-formed scar-reduction resorbable barrier micro-membranes are pre-formed and sealed in sterilized packages for subsequent use by the surgeon. Since an objective of the scar-reduction resorbable barrier micro-membranes of the present invention is to reduce sharp edges and surfaces, preformation of the membranes is believed to help facilitate, albeit to a relatively small degree, rounding of the edges for less rubbing, tissue turbulence and inflammation. That is, the surfaces and any sharp edges of the scar-reduction resorbable barrier micro-membranes are believed to be capable of slightly degrading over time in response to exposure of the membranes to moisture in the air, to thereby form rounder edges. This is believed to be an extremely minor effect. Moreover, sterilization processes (E-beam or heat) on the cut, pre-packaged and/or packaged membrane can further round any sharp edges, as can any initial heating to glass temperature of the pre-cut membranes just before implanting. Moreover, the very thin scar-reduction resorbable barrier micro-membranes of the present invention may be particularly susceptible to these phenomena, and, perhaps to a more noticeable extent, are susceptible to tearing or damage from handling, thus rendering the pre-forming of the scar-reduction resorbable barrier micro-membranes beneficial for preserving the integrity thereof.

An embodiment of the scar-reduction resorbable barrier membrane has been tested in rat studies in comparison with several scar-tissue reduction barrier gels with favorable results. Specifically, the barrier membrane material of the present invention and the scar-tissue reduction gels were inserted around the spinal column of 52 male adult Sprague-Dawley rats, each weighing 400 plus grams. A posterior midline incision was made exposing the bony posterior elements from L4 to L7, and bilateral laminectomies were performed at the L5 and L6 level using surgical loupes. Following the laminectomies, the dura was retracted medially (to the left then to the right) using a microscope to expose the disc at L5/L6, and a bilateral controlled disc injury was performed using a 26 gauge needle. After hemostasis and irrigation, an anti-inflammatory agent was applied over both laminectomy sites.

The rats were divided and treated in five groups: 1) normal controls without surgery; 2) untreated, laminectomy only; 3) those to which 0.1 cc of high molecular weight hyaluronan (HA gel) was applied to the laminectomy site; 4) those to which 0.1 cc of Adcon-L scar-tissue reduction gel was applied to the laminectomy site; and 5) those that had an insertion of a barrier membrane of the present invention over the laminectomy site. The wounds were closed in a routine manner, and the survival period was three weeks.

After termination of each of the rats, the L5 segmental nerve roots were dissected free bilaterally using an anterior approach. The segmental nerve roots were excised including the portion of the nerve root within the foramen (1 cm in length). Additionally, the dura was exposed using an anterior approach. The dura from the caudal aspect of the body of L4 to the cephalad aspect of the body of L7 was removed (1.5 center in length) including all attached scar. The samples were analyzed biochemical by extracting the fat, then vacuum drying and determining the amount of total collagen and the percent of collagen from the hydroxyproline content. The amount of total collagen was expressed in milligrams and the percent of collagen was expressed as a percent of fat free dry weight.

Each treatment group was compared to both the normal controls and the operated but untreated controls using a Fisher's multiple comparisons paired t-test. Additionally, the treatment groups were compared using a one-way analysis of variance. In the untreated, laminotomy-only specimens, the total collagen increased more than two-fold in the dura (p value of 0.0009). In the untreated group, the percent collagen increased significantly in both the dura and nerve roots (p values of 0.001 and 0.005, respectively). Treatment with HA gel (p=0.010), Adcon-L (p=0.004), or the barrier membrane of the present invention (p=0.002) significantly reduced the amount of total collagen in the dura. Likewise, the same holds true for the percent collagen where the values are: HA gel (p=0.015), Adcon-L (p=0.041), and the barrier membrane of the present invention (p=0.011). There was a trend showing that the barrier membrane of the present invention decreased approximately 50% more both in total collagen and percent collagen compared to the HA gel and Adcon-L. In the nerve roots, the amount of total collagen and a percentage of collagen was not significantly changed by treatment with any of the HA gel, Adcon-L, or barrier membrane of the present invention.

These biochemical measurements of total and percent collagen enabled obtension of quantitative data on scar formation post laminotomy. Gross findings and biochemical analysis in the model demonstrated that the untreated laminotomy scar becomes adherent to the dorsum of the dura mater, a clearly undesirable outcome. Both a single application of HA gel or Adcon-L demonstrated a beneficial effect at the level of the dura. However, the half life of HA gel is less than 24 hours, and the Adcon-L is resorbed within approximately four weeks, which suggests that further long-term studies could be conducted. Additionally, Adcon-L has the potential to delay posterior wound healing, possibly leading to wound infections and/or wound dehiscences (few of the adverse events experienced by less than 1% of the study groups per product pamphlet). On the other hand, the barrier membrane of the present invention appears to wall off the overlying muscle, potentially protecting against cellular trafficking and vascular ingrowth, and does not appear to interfere with normal posterior wound healing. A possible improvement on the results obtained by using the barrier membrane of the present invention by itself may be obtained by using the barrier membrane in conjunction with an anti-inflammatory gel agent applied, for example, beneath the barrier membrane. Additionally, the scar-tissue reduction barrier membrane may be used in combination with a fixation device for stabilizing the bone defect, such as shown in connection with the two vertebrae 20 and 22 of FIG. 1.

Figure 19:
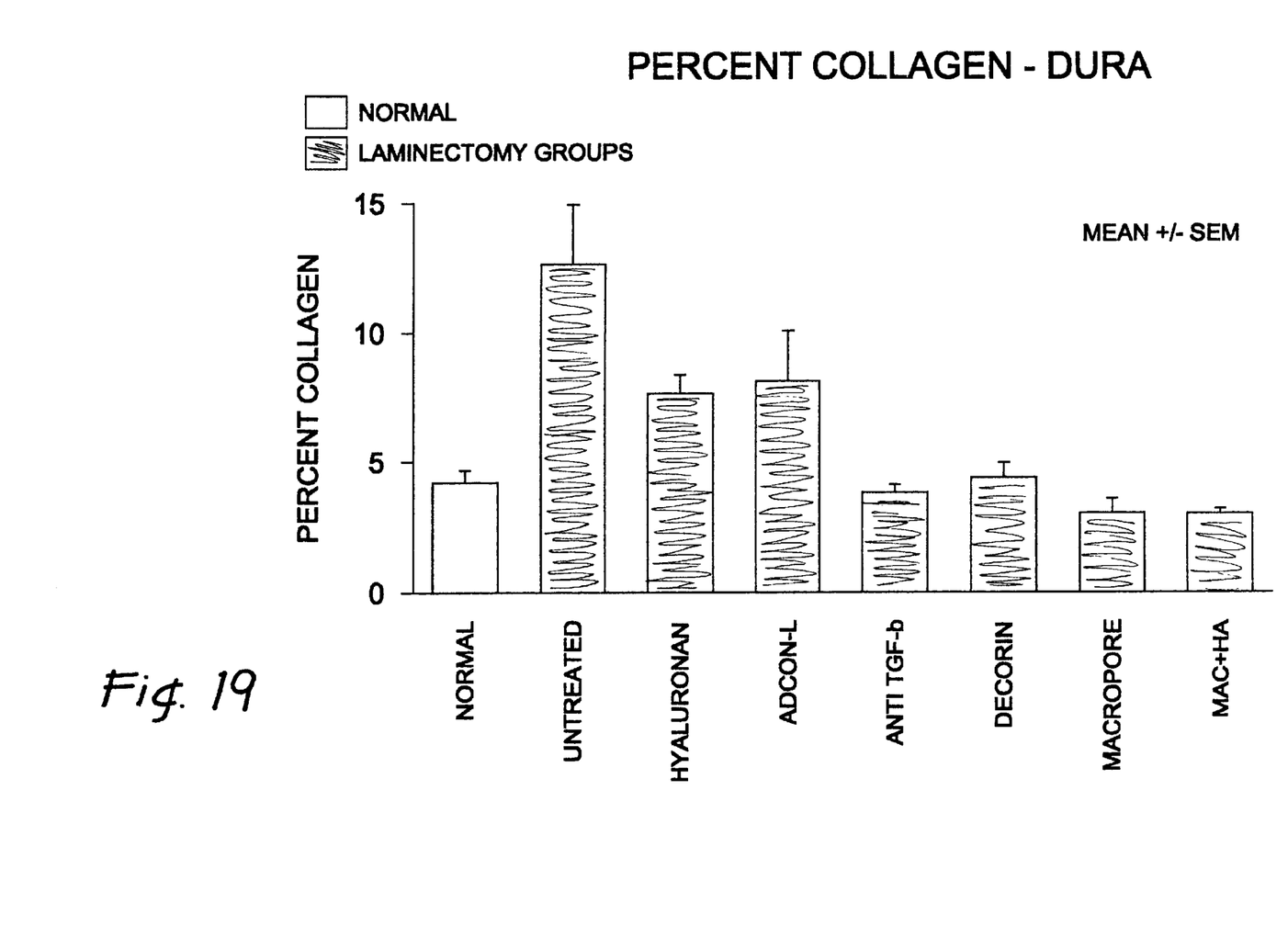
FIG. 19 is a bar graph showing the results of a study comparing the scar-reduction barrier membrane of the present invention against several other materials, and controls, indicating the percent collagen found in and around the dura following a surgical procedure after a period of about three weeks.

FIG. 19 illustrates a bar graph showing the percent collagen resulting from the aforementioned rat tests for various groups. The results for the barrier membrane of the present invention are labeled as Macropore, while the last result denoted MAC+HA is for the membrane material of the present mention in conjunction with HA gel. The results indicate that there is a marked improvement over the HA gel or Adcon-L, and significant improvement in comparison with a tissue growth factor beta and a material known as Decorin.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A resorbable scar-tissue reduction micro-membrane for attenuating a formation of post-surgical scar tissue between a healing post-surgical site and adjacent surrounding tissue following an in vivo surgical procedure on the post-surgical site, the implant having a pre-implant configuration, which is defined as a configuration of the implant immediately before the implant is formed between the post-surgical site and the adjacent surrounding tissue, the implant comprising:
   a substantially planar membrane of resorbable polymer base material having a first substantially-smooth side and a second substantially-smooth side, the substantially planar membrane of resorbable polymer base material comprising a single layer of resorbable polymer base material between the first substantially-smooth side and the second substantially-smooth side, the single layer of resorbable polymer base material having a substantially uniform composition;
   wherein a thickness of the single layer of resorbable polymer base material, measured between the first substantially-smooth side and the second substantially-smooth side, is between about 10 microns and about 300 microns;
   wherein the single layer of resorbable polymer base material is non-porous; and
   wherein the single layer of resorbable polymer base material consists essentially of a material selected from the group consisting of:
   a poly-lactide polymer; and
   a copolymer of two or more poly-lactides; and
   wherein the single layer of resorbable polymer base material is adapted to maintain a smooth-surfaced barrier between the healing post-surgical site and the adjacent surrounding tissue for a relatively extended period of time sufficient to attenuate or eliminate any formation of scar tissue between the post-surgical site and the adjacent surrounding tissue, and is adapted to be resorbed into the mammalian body within a period of approximately 18 to 24 months from an initial implantation of the implant into the mammalian body.

2. The resorbable scar-tissue reduction micro-membrane as set forth in claim 1, wherein the resorbable polymer base material is 70:30 poly (L-lactide-co-D,L-lactide).

3. The resorbable scar-tissue reduction micro-membrane as set forth in claim 1, wherein the resorbable polymer base material is poly-L-lactide.

4. The resorbable scar-tissue reduction micro-membrane set forth in claim 1, wherein the thickness is about 100 microns.

5. The resorbable scar-tissue reduction micro-membrane as set forth in claim 1, wherein the thickness is about 200 microns.

6. The resorbable scar-tissue reduction micro-membrane as set forth in claim 1, wherein the single layer of resorbable polymer base material is not fluid permeable.

7. The resorbable scar-tissue reduction micro-membrane as set forth in claim 1, wherein the resorbable scar-tissue reduction micro-membrane is impregnated with at least one of a chemotactic substance for influencing cell-migration, an inhibitory substance for influencing cell-migration, a mitogenic growth factor for influencing cell proliferation and a growth factor for influencing cell differentiation.

8. The resorbable scar-tissue reduction micro-membrane set forth in claim 1, wherein the resorbable scar-tissue reduction micro-membrane is sealed in a sterile packaging.

9. The resorbable scar-tissue reduction micro-membrane set forth in claim 8, wherein the resorbable scar-tissue reduction micro-membrane comprises a plurality of holes disposed along an edge of the resorbable scar-tissue reduction micro-membrane.

10. The resorbable scar-tissue reduction micro-membrane set forth in claim 9, wherein the edge extends around the resorbable scar-tissue reduction micro-membrane.

11. The resorbable scar-tissue reduction micro-membrane set forth in claim 10, wherein the resorbable scar-tissue reduction micro-membrane does not comprise any holes substantially away from the edge of the resorbable scar-tissue reduction micro-membrane.

12. The resorbable scar-tissue reduction micro-membrane set forth in claim 11, wherein a slit is formed in a periphery of the resorbable scar-tissue reduction micro-membrane so that the edge extends along the slit.

13. The resorbable scar-tissue reduction micro-membrane set forth in claim 10, wherein:
the resorbable scar-tissue reduction micro-membrane further comprises a plurality of holes disposed away from the edge;
each of the holes near the periphery has a first diameter;
each of the holes near the center has a second diameter; and
the first diameters are greater than the second diameters.

14. The resorbable scar-tissue reduction micro-membrane set forth in claim 13, wherein a slit is formed in a periphery of the resorbable scar-tissue reduction micro-membrane so that the edge extends along the slit.

15. The resorbable scar-tissue reduction micro-membrane set forth in claim 8, wherein the resorbable scar-tissue reduction micro-membrane comprises a slit disposed in the non-porous base material.

16. The resorbable scar-tissue reduction micro-membrane set forth in claim 8, wherein the resorbable scar-tissue reduction micro-membrane is cut to have a size and shape suitable for snugly and anatomically fitting over the dura of an exiting nerve root to thereby attenuate formation of scar tissue between the dura and surrounding muscular tissue.

17. The resorbable scar-tissue reduction micro-membrane set forth in claim 8, wherein the resorbable scar-tissue reduction micro-membrane is cut with tabs to be folded over and around an anatomic structure.

18. The resorbable scar-tissue reduction micro-membrane set forth in claim 8, wherein the resorbable scar-tissue reduction micro-membrane comprises a notch disposed in the non-porous base material.

19. The resorbable scar-tissue reduction micro-membrane set forth in claim 8, wherein the resorbable scar-tissue reduction micro-membrane comprises a plurality of notches disposed in the non-porous base material.

20. The resorbable scar-tissue reduction micro-membrane set forth in claim 1, wherein the resorbable scar-tissue reduction micro-membrane is cut to have a non-rectangular and non-circular shape and is sealed in a sterile packaging.

21. The resorbable scar-tissue reduction micro-membrane set forth in claim 2, wherein the resorbable scar-tissue reduction micro-membrane is cut to have a size and shape suitable for snugly and anatomically fitting over the dura of an exiting nerve root to thereby attenuate formation of scar tissue between the dura and surrounding muscular tissue, and is sealed in a sterile packaging.

22. The resorbable scar-tissue reduction micro-membrane set forth in claim 2, wherein the resorbable scar-tissue reduction micro-membrane is cut with tabs to be folded over and around an anatomic structure and is sealed in a sterile packaging.

23. The resorbable scar-tissue reduction micro-membrane set forth in claim 2, wherein the thickness is about 100 microns.

24. The resorbable scar-tissue reduction micro-membrane as set forth in claim 2, wherein the thickness is about 200 microns.

25. The resorbable scar-tissue reduction micro-membrane as set forth in claim 2, wherein the single layer of resorbable polymer base material is not fluid permeable.

26. The resorbable scar-tissue reduction micro-membrane as set forth in claim 2, wherein the resorbable scar-tissue reduction micro-membrane is impregnated with at least one of a chemotactic substance for influencing cell-migration, an inhibitory substance for influencing cell-migration, a mitogenic growth factor for influencing cell proliferation and a growth factor for influencing cell differentiation.

27. The resorbable scar-tissue reduction micro-membrane set forth in claim 2, wherein the resorbable scar-tissue reduction micro-membrane is sealed in a sterile packaging.

28. A resorbable scar-tissue reduction membrane for attenuating a formation of post-surgical scar tissue between a healing post-surgical site and adjacent surrounding tissue following an in vivo surgical procedure on the post-surgical site, the implant having a pre-implant configuration, which is defined as a configuration of the implant immediately before the implant is formed between the post-surgical site and the adjacent surrounding tissue, the implant comprising:
a substantially planar membrane of resorbable polymer base material having a first substantially-smooth side and a second substantially-smooth side, the substantially planar membrane of resorbable polymer base material comprising a layer of resorbable polymer base material between the first substantially-smooth side and the second substantially-smooth side, the layer of resorbable polymer base material having a substantially uniform composition;
wherein a thickness of the layer of resorbable polymer base material, measured between the first substantially-smooth side and the second substantially-smooth side, is between about 10 microns and about 300 microns;
wherein the layer of resorbable polymer base material is non-porous; and
wherein the layer of resorbable polymer base material consists essentially of a material selected from the group consisting of:
a poly-lactide; and
a copolymer of two or more poly-lactides; and
wherein the substantially planar membrane of resorbable polymer base material is sealed in a sterile package.

29. The resorbable scar-tissue reduction micro-membrane set forth in claim 28, wherein the resorbable scar-tissue reduction micro-membrane is cut to have a non-rectangular and non-circular shape and is cut to anatomically fit over and protect an exiting nerve root.

30. The resorbable scar-tissue reduction micro-membrane set forth in claim 28, wherein the resorbable scar-tissue reduction micro-membrane is cut to have a non-rectangular and non-circular shape and is cut with tabs to be folded over and around and to protect an exiting nerve root.

31. The resorbable scar-tissue reduction micro-membrane set forth in claim 28, wherein the resorbable scar-tissue reduction micro-membrane is cut to have a non-rectangular and non-circular shape.

32. The resorbable scar-tissue reduction micro-membrane set forth in claim 28, wherein the membrane comprises a substantially planar membrane of resorbable polymer base material having a first substantially-smooth side and the second substantially-smooth side, the substantially planar membrane of resorbable polymer base material comprising a single layer of resorbable polymer base material between the first substantially-smooth side and the second substantially-smooth side, the single layer of resorbable polymer base material having a substantially uniform composition.

* * * * *